United States Patent [19]

Huth et al.

[11] Patent Number: 5,254,563
[45] Date of Patent: Oct. 19, 1993

[54] BETA-CARBOLINES, PROCESS FOR THEIR PRODUCTION AND THEIR USE IN PHARMACEUTICAL AGENTS

[75] Inventors: Andreas Huth; Martin Kruger; Dieter Rahtz; Dieter Seidelmann; Ralph Schmiechen; Lechoslaw Turski, all of Berlin, Fed. Rep. of Germany; John S. Andrews, EP, Oss, Netherlands; Herbert H. Schneider, Berlin, Fed. Rep. of Germany

[73] Assignee: Schering Aktiengesellschaft, Berlin and Bergkamen, Fed. Rep. of Germany

[21] Appl. No.: 773,659

[22] PCT Filed: Dec. 19, 1990

[86] PCT No.: PCT/DE90/00982
§ 371 Date: Oct. 23, 1991
§ 102(e) Date: Oct. 23, 1991

[87] PCT Pub. No.: WO91/09858
PCT Pub. Date: Jul. 11, 1991

[30] Foreign Application Priority Data

Dec. 23, 1989 [DE] Fed. Rep. of Germany ....... 3943225

[51] Int. Cl.[5] ................. C07D 471/04; A61K 31/435

[52] U.S. Cl. ...................................... 514/292; 546/14; 546/85; 546/86

[58] Field of Search ............................ 546/85, 86, 14; 514/292

[56] References Cited

FOREIGN PATENT DOCUMENTS 0054507 6/1982 European Pat. Off. .............. 546/85
2619817 8/1988 France ................................. 546/85

Primary Examiner—C. Warren Ivy
Assistant Examiner—Zinna N. Davis
Attorney, Agent, or Firm—Millen, White, Zelano & Branigan

[57] ABSTRACT

Compounds of formula I

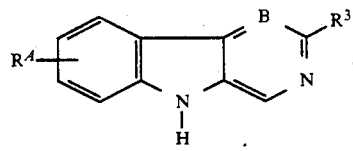

in which $R^4$, B (which is $CR^4$) and $R^3$ and have the meaning indicated in the application, as well as their production and their use in pharmaceutical agents, are described.

8 Claims, No Drawings

BETA-CARBOLINES, PROCESS FOR THEIR PRODUCTION AND THEIR USE IN PHARMACEUTICAL AGENTS

The invention relates to new beta-carbolines, their production and use in pharmaceutical agents.

From numerous publications, such as, for example, from EP-A-54507, it is known that beta-carbolines influence the central nervous system and are suitable as psychopharmacological agents. Surprisingly, it was shown that the beta-carbolines, substituted in 3-position according to the invention, are bio-available over a longer period and at the same time exhibit a good affinity for the benzodiazepine receptors.

The compounds according to the invention have general formula I

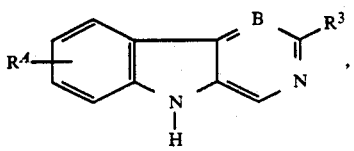

I in which

R$^A$ means halogen, —CHR$^1$-R$^2$, phenyl or OR$^5$ and can be single or double and R$^1$ represents hydrogen or C$_{1-4}$alkyl, R$^2$ represents hydrogen, C$_{1-4}$ alkyl, —O—C$_{1-4}$ alkyl or an optionally substituted phenyl, benzyl or phenoxy radical, and R$^5$ represents hydrogen, tri-C$_{1-4}$-alkylsilyl, C$_{1-4}$alkyl, C$_{3-7}$cycloalkyl or an optionally substituted phenyl, benzyl or hetaryl radical and B is nitrogen or CR$^4$ and R$^4$ is hydrogen, C$_{1-4}$alkyl or C$_{1-4}$alkoxy-C$_{1-2}$alkyl and R$^3$ is —CO—R or —CHOH—R and R represents an optionally substituted monocyclic or bicyclic aryl or hetaryl radical or a C$_{3-10}$cycloalkyl or bicycloalkyl radical as well as their isomers and acid addition salts.

Substituent R$^A$ can be in the A-ring in 5- to 8-position, preferably in 5-, 6- or 7-position.

Alkyl in each case contains both straight-chain and branched-chain radicals, such as, for example, methyl, ethyl, propyl, isopropyl, butyl, isobutyl, sec-butyl and tert-butyl.

By halogen is understood, respectively, fluorine, chlorine, bromine and iodine.

Cycloalkyl in each case can stand for cyclopropyl, cyclobutyl, cyclopentyl, cyclohexyl, cycloheptyl, cyclooctyl, cyclononyl and 2-methyl-cyclopropyl, and 3-5 carbon atoms are preferred for substituent R$^5$.

If R$^5$ means a hetaryl radical, the latter is 5- or 6-membered and contains 1-2 heteroatoms, such as nitrogen, oxygen and/or sulfur. For example, the following 5- and 6-ring heteroaromatic compounds can be mentioned: pyridine, pyrimidine, pyrazine, pyridazine, furan, thiophene, pyrrole, thiazole, imidazole.

Heterocycles containing nitrogen and substituted with halogen can optionally be considered as preferred hetaryl radicals R$^5$.

The substituent of phenyl, benzyl and hetaryl radical R$^5$ can be single to triple in any position. Suitable substituents are halogens, nitro, cyano, C$_{1-4}$alkyl, C$_{1-4}$alkoxy, amino and C$_{1-4}$ alkoxycarbonyl, and in particular fluorine, chlorine and bromine are preferred.

As substituents of phenyl, benzyl and phenoxy radical R$^2$, the substituents of the aromatic compounds, mentioned for R$^5$, are suitable, in particular halogens such as chlorine and bromine.

The aryl and hetaryl radical in R$^3$ can be present as a monocyclic or bicyclic compound and can contain 5–12 ring atoms, preferably 5–9 ring atoms, such as, for example, phenyl, biphenylyl, naphthyl, indenyl as aryl radical, and thienyl, furyl, pyranyl, pyrrolyl, pyrazolyl, pyridyl, pyrimidinyl, pyridazinyl, oxazolyl, isooxazolyl, thiazolyl, isothiazolyl, quinolyl, isoquinolyl, benzo[1]thienyl, benzofuryl as hetaryl radical with 1-2 heteroatoms, such as sulfur, oxygen and/or nitrogen.

The substituent of aryl and hetaryl radical R can be single to double and can be halogen, C$_{1-4}$ alkyl, C$_{1-4}$ alkoxy, cyano, amino or nitro, and C$_{1-4}$alkyl, C$_{1-4}$alkoxy and amino are preferred.

By a bicycloalkyl radical R is understood, for example, bicycloheptyl and bicyclooctyl.

If a chiral center is present, the compounds of formula I can be present in the form of diastereomers and their mixtures.

The physiologically compatible acid addition salts are derived from the known inorganic and organic acids, such as, for example, hydrochloric acid, hydrobromic acid, sulfuric acid, phosphoric acid, formic acid, acetic acid, benzoic acid, maleic acid, fumaric acid, succinic acid, tartaric acid, citric acid, oxalic acid, glyoxylic acid as well as from alkanesulfonic acids and arylsulfonic acids, such as, for example, methanesulfonic acid, ethanesulfonic acid, benzenesulfonic acid, p-toluenesulfonic acid, i.a.

As especially preferred embodiments for R, the cycloalkyls, mentioned at the beginning, with 3–5 carbon atoms as well as optionally substituted phenyl, biphenyl, naphthyl and thienyl can be considered.

The compounds of formula I as well as their acid addition salts are usable because of their affinity for benzodiazepine receptors as pharmaceutical agents and have antagonistic, inversely agonistic and agonistic effects on the properties known of the benzodiazepines. At the same time, the compounds according to the invention show an extended duration of action.

By the example of the 3-benzoyl derivative in comparison with the 3-carboxylic acid phenyl ester derivative, it can be gathered from the table below that the compounds according to the invention not only exhibit a higher stability relative to hepatic enzymes, but also have a better affinity, especially a better in vivo affinity, for benzodiazepine receptors. The affinity is determined by examining the displacement capacity of radioactively-labeled flunitrazepam from the benzodiazepine receptors.

The ED$_{50}$ value represents the dose of a test substance, which brings about a reduction of the specific binding of the flunitrazepam to the benzodiazepine receptor in a living brain to 50% of the control value.

The in vivo test is performed as follows:

The test substance is injected in varying doses and normally intraperitoneally in groups of mice. After 15 minutes, the $^3$H-flunitrazepam is administered intravenously to the mice. After another 20 minutes, the mice are killed, their forebrains are removed, and the radioactivity specifically bound to the brain membranes is measured by scintillation counting. The ED$_{50}$ value is determined from the dose-effect curves.

The metabolic stability is determined by a homogenate of hepatic tissue in physiological common salt solution being incubated with the test substance for 0 or 2 hours at 37° C. Then, the incubation batch is extracted and the content of test substance in the extract is determined by HPLC/fluorimetry. The substance remaining after 2 hours in comparison with 0 hours is expressed in percent stability.

| Inhibition of the $H^3$-BD binding | Metabolic Stability |
|---|---|
| In vivo $ED_{50}$ mg/kg | Human liver homogenate 2 hours at 37° C. |
| A  5.0 | 72% |
| B  greater than 90 | |

A = 6-benzyloxy-4-methoxymethyl-3-benzoyl-beta-carboline
B = 6-benzyloxy-4-methoxymethyl-beta-carboline-3-carboxylic acid phenyl ester The compounds according to the invention are further distinguished by anxiolytic and anticonvulsive effectiveness.

To examine the anxiolytic effect, the compounds are tested in the 4-plate test according to the method of Boissier et al., Eur. J. Pharmacol. 4, 145–150 (1968). In this case, the minimal effective dose (MED) is indicated, which increases the locomotor activity of the afflicted mice after intraperitoneal treatment. A reduction of the activity in the 4-plate test without being afflicted indicates sedative properties.

The compounds of formula I are suitable in particular for treatment of anxiety accompanied by depressions, epilepsy, sleep disturbances, spasticities and muscle relaxation during anesthesia and also show amnestic or memory-promoting properties.

To use the compounds according to the invention as pharmaceutical agents, the latter are put in the form of a pharmaceutical preparation, which, besides the active ingredient for the enteral or parenteral administration, contains suitable pharmaceutical, organic or inorganic inert vehicles, such as, for example, water, gelatin, gum arabic, lactose, starch, magnesium stearate, talc, vegetable oils, polyalkylene glycols, etc.

The pharmaceutical preparations can be present in solid form, for example, as tablets, coated tablets, suppositories, capsules or in liquid form, for example, as solutions, suspensions or emulsions. Optionally, they also contain auxiliary agents, such as preservatives, stabilizers, wetting agents or emulsifiers, salts to change the osmotic pressure or buffers.

For parenteral administration, in particular injection solutions or suspensions, in particular aqueous solutions of the active compounds in polyhydroxyethoxylated castor oil, are suitable.

As vehicle systems, surface-active auxiliary agents such as salts of the bile acids or animal or plant phospholipids, but also their mixtures as well as liposomes or their components, can also be used.

For oral application, in particular tablets, coated tablets or capsules with talc and/or hydrocarbon vehicles or binding agents, such as, for example, lactose, corn starch or potato starch, are suitable. The application can also take place in liquid form, such as, for example, as juice, to which a sweetener is optionally added.

The compounds according to the invention are introduced in a dosage unit of 0.05 to 100 mg of active substance in a physiologically compatible vehicle.

The compounds according to the invention are generally used in a dose of 0.1 to 300 mg/day, preferably 0.1 to 30 mg/day, especially preferably 1–20 mg/day, for example, as anxiolytic agents analogous to diazepam.

The production of the compounds according to the invention can be performed according to methods known in the art. For example, compounds of formula I are attained, in that compounds of formula II

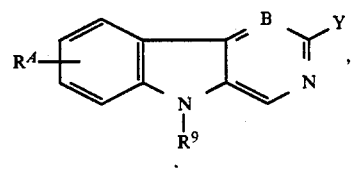

in which $R^4$ and B have the above-mentioned meaning and
$R^9$ is hydrogen or a protecting group and
Y is cyano or —CO—Z and
Z is hydrogen, $C_{1-4}$alkoxy or an acid derivative, are reacted with a metallo-organic compound R-Me and then optionally a trialkylsilyl group is cleaved to the hydroxy group is etherified to $R^4$=$OR^5$ or $R^3$ meaning —CH—OH—R is oxidized to the ketone or the protecting groups are cleaved or the isomers are separated or the acid addition salts are formed.

For example, a Grignard compound, such as R-Mg-halogen, or a lithium-organic compound R-Li is suitable as a metallo-organic compound. For the reaction with the metallo-organic compound, suitable acid derivatives are, for example, carboxylic acid amides —$NR^7R^8$, in which $R^7$ represents $C_{1-4}$alkyl and $R^8$ represents $C_{1-4}$alkyl or $C_{1-4}$alkoxy or $R^7$ and $R^8$ together with the nitrogen atom form an imidazole.

The reaction with the metallo-organic compound can be performed at temperatures of $-70°$ C. up to room temperature in aprotic polar solvents, such as cyclic and acyclic ethers or hydrocarbons. For example, as a suitable solvent, there can be mentioned diethyl ether, tetrahydrofuran, dioxane, toluene, hexane, i.a.

As protecting groups $R^9$, all protecting groups usually used are suitable, such as, for example, alkyl, alkanoyl, aralkyl, arylsulfonyl, alkylsulfonyl or silyl radicals, and sulfonyls, such as tosyl and mesyl and trialkylsilyls, such as tert-butyldimethylsilyl, trimethylsilyl and tert-butoxycarbonyl, are preferred.

If a protecting group $R^9$ or tri-$C_{1-4}$alkylsilyloxy group $R^4$ is present in the compounds of formula I, the latter can be cleaved with the usual methods, such as, by treatment with bases, such as sodium or potassium hydroxide or alcoholate, or acids, such as dilute mineral acid, trifluoroacetic acid or tetrabutylammonium fluoride, optionally during the working up of the reaction mixture, at room temperature or higher temperature.

If the compounds according to the invention with $R^4$ meaning OH are etherified, the methods described in EP-237467, EP-A-234173 and EP-A-130140 can be used, by, for example, a reactive derivative $R^5x$, in which x is halogen, tosylate, mesylate or triflate, being reacted in the presence of a base in a polar solvent.

If the compounds of formula I contain $R^3$ meaning a —CHOH—R group, the latter can be oxidized to a —CO—R group, by being oxidized optionally in the presence of an organic base such as pyridine, triethylamine with oxalyl chloride or with an oxidizing agent such as manganese dioxide, pyridine chlorochromate, chromium oxide, iron (III) chloride or according to the Oppenauer method or by being dehydrogenated in the presence of a copper catalyst. Also, oxidation with azodicarboxylic acid ester is possible, for example, analogously to F. Yoneda et al., J. Org. Chem. 32, 727 (1967).

The reaction can be performed at room temperature or higher temperature up to boiling temperature of the reaction mixture in an inert solvent, such as chlorinated hydrocarbons, hydrocarbons, acetone, alcohols such as tert-butanol.

The mixture of isomers can be separated according to the usual methods, such as, for example, crystallization, chromatography or salt formation in the diastereomers or enantiomers.

For the formation of physiologically compatible acid addition salts, a compound of formula I is dissolved, for example, in a little alcohol and mixed with a concentrated solution of the desired acid.

In so far as the production of the initial compounds is not described, their method of production is known or analogous to that of known compounds or the latter can be produced analogously to processes described here.

For example, the production of the 3-formyl derivative of formula II can take place analogously to the methods described in Ep-A-216541 and EP-A-305322. The production of 3-carboxylic acid esters and their reactive acid derivatives is described, for example, in EP-A-54507, EP-A-237467, EP-A-234173, EP-A-137390, EP-A-23966 and EP-A-222693. The production of the nitriles takes place, for example, according to the process described in EP-A-234137.

The following examples are to explain the process according to the invention.

Production of the initial compounds

A)

6-Benzyloxy-4-methoxymethyl-bea-carboline-3-carboxylic acid dimethylamide

Dimethylamine was introduced for 5 minutes in a solution of 1.0 g of 6-benzyloxy-4-methoxymethyl-beta-carboline-3-carboxylic acid imidazolide in 25 ml of dimethylformamide. Then, it was diluted with ethyl acetate and washed with water, dried, filtered and concentrated by evaporation. The residue was recrystallized from ethyl acetate and yielded 680 mg of the title compound of melting point of 174°-176° C.

B)

6-Benzyloxy-4-methoxymethyl-beta-carboline-3-carboxylic acid imidazolide 1.34 g of 6-benzyloxy-4-methoxymethyl-beta-carboline-3-carboxylic acid was mixed in 50 ml of absolute tetrahydrofuran at room temperature with 45 ml of a freshly prepared 0.27 molar thionyl diimidazole solution in tetrahydrofuran and stirred for 2 hours with exclusion of moisture. After distilling off the solvent, it was taken up in ethyl acetate/water, washed twice with water and once with saturated sodium chloride solution. The ethyl acetate phase was dried, concentrated by evaporation and the resulting crude product was absorptively precipitated with ethyl acetate.

1.31 g of the title compound with melting point 184°-185° C. was obtained.

Analogously, there are produced:
6-(2-pyrazinyloxy -4-methoxymethyl-beta-carboline-3-carboxylic acid imidazolide
5-(4-chlorophenoxy)-4-methoxymethyl-beta-carboline-3-carboxylic acid imidazolide
5-(4-fluorobenzyloxy)-4-methoxymethyl-beta-carboline-3-carboxylic acid imidazolide

EXAMPLE 1

6-Benzyloxy-3-cycloproxylcarbonyl-4-methoxymethyl-betacarboline 18 ml of a 0.5 molar solution of cyclopropylmagnesium bromide in tetrahydrofuran was instilled in 618 mg of 6-benzyloxy-4-methoxymethyl-beta-carboline-3-carboxylic acid imidazolide in 45 ml of absolute tetrahydrofuran at −6° to −10° C. in about 10 minutes and stirred for 1 hour under ice cooling. After 16 hours of reaction time at room temperature, it was weakly acidified with dilute HCl solution, concentrated by evaporation and extracted with methylene chloride. The organic phase was washed with water, saturated sodium bicarbonate solution and saturated sodium chloride solution, dried and concentrated by evaporation. 133 mg of the title compound with melting point of 133° C. was obtained by column chromatography on silica gel with methylene chloride/ethanol 2:1 and recrystallization from ethyl acetate/petroleum ether.

Analogously, there are obtained:
6-benzyloxy-4-methoxymethyl-3-(1-naphthyl)-carbonyl-beta-carboline, melting point 223°-224 C. (ethyl acetate, ethanol hexane)
6-benzyloxy-3-(2-methylcyclopropylcarbonyl)-4-methoxymethyl-beta-carboline
5-(4-chlorophenoxy)-3-cyclopropylcarbonyl-4-methoxymethyl-beta-carboline
6-benzyloxy-3-(cyclobutylcarbonyl)-4-methoxymethyl-beta-carboline, melting point 153°-154 C. (ethyl acetate, hexane)
6-(2-pyrazinyloxy)-3-cyclopropylcarbonyl-4-methoxymethyl-beta-carboline, melting point 167°-169° C. (ethyl acetate/hexane)
5-(4-fluorobenzyloxy-3-cyclopropylcarbonyl)-4-methoxymethylbeta-carboline

EXAMPLE 2

6-Benzyloxy-4-methoxymethyl-3-benzoyl-beta-carboline

A solution of 1.09 g of 6-benzyloxy-4-methoxymethyl-9-tosyl-beta-carboline-3-carboxylic acid isopropyl ester isopropyl ester in 20 ml of absolute tetrahydrofuran was mixed at −60° C. under argon with 2.1 ml of a 1.08 molar phenyllithium solution in ether/hexane, stirred for 1 hour at −60° C. and then heated slowly to room temperature. After 3 hours of reaction time at room temperature, it was acidified with nHCl and the solvent was distilled off. After taking up in ethyl acetate/water, the organic phase was separated, washed with saturated sodium chloride solution, dried and concentrated by evaporation. 435 mg of the title compound was obtained by crystallization of ethanol/petroleum ether, melting point 167°-168° C.

Analogously, there are obtained:
6-benzyloxy-4-methoxymethyl-3-(thiophen-2-yl)-beta-carboline, melting point 165° C. (ethyl acetate/petroleum ether)
6-benzyloxy-4-methoxymethyl-3-(2-methoxybenzoyl)-beta-carboline, melting point 145°-146 C. (ethyl acetate/petroleum ether)
3-benzoyl-6,7-dimethoxy-4-ethyl-beta-carboline, melting point 182°-184° C. (methylene chloride/ethanol), from 6,7-dimethoxy-4-ethyl-9-tosyl-beta-carboline-3-carboxylic acid ethyl ester, 3-benxyl-5-bezyloxy-4- methoxymethyl-beta-carboline, melting point 195°-198° C. (cyclohexane/ethyl acetate), from 5-oxy-4-methoxymethyl-9-tosyl-beta-carbolxylic acid ethyl ester, melting point 149°-150° C. (ethyl acetate)

3-benzoyl-5-isopropoxy-4-methyl-beta-carboline, melting point 234°-235° C. (cyclohexane/ethyl acetate), from 5-isopropoxy-4-methyl-9-tosyl-beta-carboline-3carboxylic-3-carboxylic acid methyl ester, melting point 160°-161° C. (isopropanol) melting point 197°-198° C. (ethyl acetate)

3-benzoyl-5-(4-fluorobenzyloxy)-4-methoxymethyl-beta-carboline, melting point 213°-214° C., from 5-(4-fluorobenzyloxy)-4-methoxymethyl-9-tosyl-beta-carboline -3-carboxylic acid ethyl ester 149°-150° C.

3-[(2-methyl)-benzoyl]-6-benzyloxy-4-methoxymethyl-beta-carboline, melting point 164° C. (ethyl acetate, ethanol, hexane)

3-(4-phenylbenzoyl)-6-benzyloxy-4-methoxymethyl-beta-carboline, melting point 108°-109° C. (ethyl acetate, ethanol, hexane)

3-benzoyl-4-methoxymethyl-5-(4-chlorophenoxy)-beta-carboline, melting point 238°-240°C. (methylene chloride, ethyl acetate, hexane), from 5-(4-chlorophenoxy)-4-methoxymethyl-9-tosyl-beta-carboline-3-carboxylic acid isopropyl ester of melting point 185°-187° C.

EXAMPLE 3

2-Benzoyl-8-phenoxy-5H-pyrimido[5,4-b]indole

Analogously to example 2, the title compound is obtained from 8-phenoxy-5-tosyl-5H-pyrimido[5,4-b]indole-2-carboxylic acid ethyl ester, melting point 251°-253° C. (ethyl acetate).

Production of the initial material:

Analogously to the synthesis described by K. Clarke, W. Richard and R. M. Scrowston, J. Chem. Res. 1980 (2) 833-847, 2-amino-5-phenoxy-benzonitrile is converted to 3-amino-4-phenoxy-1-tosylindole-2-carbonitrile, which, analogously to the process described in EP-A-115248, is converted to 8-phenoxy-5-tosyl-5H-pyrimido[5,4-b]indole-2-carboxylic acid ethyl ether with melting point 136°-139° C. (ethanol).

EXAMPLE 4

3-Benzoyl-5-ethoxymethyl-beta-carboline

Analogously to example 2, the title compound is obtained from 5-ethoxymethyl-9-tosyl-beta-carboline-3-carboxylic acid ethyl ester, melting point 195°-197° C. (ethyl acetate).

Production of the initial material:

By tosylation of 5-ethoxymethyl-beta-carboline-3-carboxylic acid ethyl ester, known from Ep-110813, melting point 142°-143° C. (ethanol).

EXAMPLE 5

3-Benzoyl-4,5-diethyl-beta-carboline

Analogously to example 2, the title compound is obtained from 4,5-dimethyl-9-tosyl-beta-carboline-3-carboxylic acid ethyl ester, melting point 208°-209° C. (ethyl acetate).

The production of the initial compounds takes place by known esterification and tosylation of 4,5-dimethyl-beta-carboline-3-carboxylic acid.

EXAMPLE 6

3-Benzoyl-5-ethoxymethyl-4-methoxymethyl-beta-carboline

Analogously to example 2, the title compound is obtained from 5-ethoxymethyl-4-methoxymethyl-9-tosyl-beta-carboline-3-carboxylic acid ethyl ester, melting point 180°-182° C. (ethanol).

The production of the initial material takes place by tosylation of 5-ethoxymethyl-4-methoxymethyl-beta-carboline-3-carboxylic acid ethyl ester known from EP-A-161575, melting point 90°-92° C. (ethanol).

EXAMPLE 7

3-Benzoxy-4-methoxymethyl-6-triisoproylsilyloxy-beta-carboline

A solution of 230 mg of 4-methoxymethyl-9-tosyl-6-triisopropylsilyloxy-beta-carboline-3-carboxylic acid isopropyl ester in 3.5 ml of absolute tetrahydrofuran was mixed at $-60°$ C. under argon with 0.38 ml of a 1.08 molar phenyllithium solution in ether/hexane, stirred for 1 hour at $-60°$ C. and heated slowly to room temperature. After 16 hours of standing at room temperature, the reaction mixture was mixed with N-acetic acid/ethyl acetate, the ethyl acetate phase was washed with water and saturated sodium chloride solution, dried and concentrated by evaporation. After column chromatography on silica gel with cyclohexane/ethyl acetate 1:1 as eluant, 69 mg of title compound was obtained.

Production of the initial material

A)

4-Methoxymethyl-6-(tripsoropylsilyloxy)-beta-carboline-carboxylic acid isopropyl ester 314 mg of 6-hydroxy-4-methoxymethyl-beta-carboline-3-carboxylic acid isopropyl ester was stirred in 20 ml of dichloromethane with 61 mg of 4-dimethylaminopyridine, 0.31 ml of triethylamine and 425 mg of chlorotriisopropylsilane for 7 hours at room temperature. Then, it was washed with water and saturated common salt solution, the organic phase was dried and concentrated by evaporation. After purification of the crude product on a silica gel column with dichloromethane/ethanol 10:1 as eluant and recrystallization from ether/petroleum ether, 392 mg of the desired compound was obtained, melting point 144°-145° C.

B)

4-Methoxymethyl-9-tosyl-6-(triisopropylsilyloxy)-beta-carboline-3-carboxylic acid isopropyl ester 1 g of 4-methoxymethyl-6-(triisopropylsilyloxy)-beta-carboline-3-carboxylic acid isopropyl ester, 132 mg of 4-dimethylaminopyridine and 0.45 ml of triethylamine were mixed in 10 ml of dichloromethane at about 4° C. with 615 m of tosyl chloride and then stirred at room temperature for 1 hour. After 16 hours of standing at room temperature, it was diluted with dichloromethane and washed with saturated sodium bicarbonate solution and saturated sodium chloride solution. After chromatography on silica gel in the system of cyclohexane/ethyl acetate 1:1, 1.32 g of the title compound was obtained from the isolated organic phase.

EXAMPLE 8

3-Benzoyl-6-hydroxy-4-methoxymethyl-beta-carboline 530 mg of 3-benzoyl-6-triisopropylsilyloxy-4-methoxymethyl-beta-carboline was dissolved in 7.5 ml of absolute tetrahydrofuran and stirred for 0.5 hour under argon at room temperature after adding 1.1 ml of a 1.1 molar tetrabutylammonium fluoride solution in tetrahydrofuran. After adding ethyl acetate, the organic phase was washed with saturated common salt solution, dried and concentrated by evaporation. 315 mg of the title compound was obtained after absorptive precipitation with ethyl acetate/petroleum ether, melting point 258° C.

EXAMPLE 9

3-Benzoyl-6-(5-bromopyridin-2-yloxy)-4-methoxymethyl-beta-carboline 332 mg of 3-benzoyl-6-hydroxy-4-methoxymethyl-beta-carboline and 130 mg of potassium hydroxide powder were mixed in 3 ml of dimethyl sulfoxide under argon with 285 mg of 2,5-dibromopyridine in 1 ml of dimethyl sulfoxide and heated for 1 hour to 90°-95° C. The reaction mixture was poured on ice water, acidified with 1N-acetic acid to pH 5 and shaken out with ethyl acetate. The ethyl acetate phase was washed with saturated common salt solution, dried on magnesium sulfate and concentrated by evaporation. After chromatography on silica gel with dichloromethane/ethyl acetate 1:1 as eluant and recrystallization from the main fraction from ethyl acetate/petroleum ether, the title compound with melting point 193°-194° C. was obtained.

EXAMPLE 10

6-Benzyloxy-3-(1-hydroxy-1-phenylmethyl)-4-methoxymethyl-beta-carboline 300 mg of 6-benzyloxy-3-(1-hydroxy-1-phenylmethyl)4methoxymethyl-9-(4-methylphenylsulfonyl)-beta-carboline was added a sodium methylate solution of 50 mg of 80% sodium hydride and 30 ml of absolute ethanol and refluxed for 2 hours under argon. After distilling off the solvent, the residue was taken up in ethyl acetate and washed with saturated sodium chloride solution. After column chromatography on silica gel in the system of dichloromethane/ethanol 12:1, 211 mg of the title compound was obtained after recrystallization from ethyl acetate/petroleum ether from the ethyl acetate phase dried on magnesium sulfate and concentrated by evaporation, melting point 190°-191° C.

Analogously, there are obtained:
6-Benzyloxy-3-(1-hydroxy-1-cyclopentylmethyl)-4-methoxymethyl-beta-carboline Production of the initial material 6-Benzyloxy-3-(1-hydroxy-1-phenylmethyl)-4-methoxymethyl-9-(4-methylphenylsulfonyl)-beta -carboline A solution of 1.0 g of 6-benzyloxy-3-formyl-4-methoxymethyl -9-(4-methylphenylsulfonyl)-beta-carboline in 60 ml of absolute tetrahydrofuran was mixed at −60° C. under argon with 2.4 ml of a 1.08 molar phenyllithium solution in ether/hexane, stirred for 1 hour at −60° C. and then heated slowly to room temperature. After taking up in ethyl acetate/water, the organic phase was separated, washed with saturated sodium chloride solution, dried and concentrated by evaporation. After column chromatography on silica gel with the eluants dichloromethane/ethanol 15:1 and cyclohexane/ethyl acetate 1:1, 717 mg of the title compound was obtained with melting point 169°-171° C.

Analogously, there are obtained:
With cyclopentylmagnesium bromide, 6-benzyloxy-3-(1-hydroxy-1-cyclopentylmethyl)-4-methoxymethyl-9-(4 -(4-methylphenylsulfonyl)-beta-carboline, melting point 146°-147° C. (ethyl acetate, ethanol, hexane).

EXAMPLE 11

3-Benzoyl-5-(2-chlorophenoxymethyl)-4-methoxymethyl-beta-carboline

Analogously to example 2, the title compound is obtained from 5-(2-chlorophenoxymethyl)4-methoxymethyl-9-tosyl-betacarboline-3-carboxylic acid ethyl ester, melting point 149°-152° C. (ethanol).

Production of the initial material a) 4-(2-Chlorophenoxy)-methylindole

A solution of 4-hydroxymethylindole (1.0 g) in tetrahydrofuran (10 ml) is instilled in a solution of triphenylphosphine (2.92 g), 2-chlorophenol (1.43 g) and azodicarboxylic acid diethyl ester (1.49 g) in tetrahydrofuran (50 ml). After a three-hour stirring of the reaction mixture, it is worked up in the usual way and the crude product is chromatographed, melting point 138°-140° C. (cyclohexane).

b) 5-(2-Chlorophenoxy)-methyl-4-methoxymethyl-beta-carboline-3-carboxylic acid ethyl ester Production analogously to F. Neef et al, 1983 Heterocyclus 20, 1295-1313 (method a), melting point 67°-68° C.

c) 5-(2-Chlorophenoxy)-methyl-4-methoxymethyl-9-tosyl-beta-carboline-3-carboxylic acid ethyl ester Preparation analogously to example 7B, melting point 149°-152° C. (ethanol)

EXAMPLE 12

6-Benzyloxy-3-cyploproxylcarbonyl-4-methoxymethyl-beta-carboline 50 mg of 6-benzyloxy-3-(1-hydroxy-1-phenylmethyl)-4-methoxymethyl-beta-carboline is stirred in 10 ml of methylene chloride with 300 mg of manganese dioxide for 1 hour at room temperature. After suctioning off on diatomaceous earth, the filtrate was concentrated by evaporation and the residue was chromatographed on silica gel with methylene chloride : ethyl acetate =2:1. 20 mg of the title compound is obtained.

We claim:

1. A compound of formula I

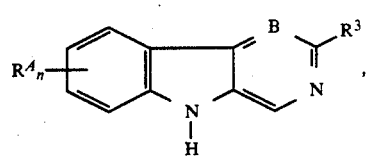

wherein
$R^4$ is halogen, —$CHR^1$—$R^2$, phenyl or $OR^5$;
n is 1 or 2;
$R^1$ is hydrogen or $C_{1-4}$ alkyl;
$R^2$ is hydrogen, $C_{1-4}$ alkyl, —O—$C_{1-4}$ alkyl or substituted or unsubstitued phenyl, benzyl or phenoxy radical;
$R^5$ is hydrogen, tri-$C_{1-4}$ alkylsilyl, $C_{1-4}$ alkyl, $C_{3-7}$ cycloalkyl or substituted or unsubstituted phenyl, benzyl or hetaryl radical;
B is $CR^4$;
$R^4$ is unsubstituted or substituted monocylic or bicyclic aryl or hetaryl radical or a $C_{3-10}$ cycloalkyl or bicycloalkyl radical as well as their isomers; or an acid addition salt thereof.

2. 6-Benzyloxy-4-methoxymethyl-3-benzoyl-beta-carboline, 6-(5-bromopyridin-2-yloxy)-4-methoxymethyl-3-benzoyl-beta-carboline, or an acid addition salt thereof.

3. A pharmaceutical agent comprising a compound of claim 1 and a pharmaceutically acceptable carrier.

4. A pharmaceutical agent comprising a compound of claim 2 and a pharmaceutically acceptable carrier.

5. A compound according to claim 1, wherein $R^2$ is a substituted phenyl, benzyl, or phenoxy substituted by halogen, nitro, cyano, $C_{1-4}$ alkyl, $C_{1-4}$ alkoxy, amino or $C_{1-4}$ alkoxycarbonyl group.

6. A compound according to claim 1, wherein $R^5$ is a substituted phenyl, benzyl or hetaryl substituted by halogen, nitro, cyano, $C_{1-4}$ alkyl, $C_{1-4}$ alkoxy, amino or $C_{1-4}$ alkoxycarbonyl group.

7. A compound according to claim 1, wherein R is a substituted aryl or hetaryl substituted by a halogen, $C_{1-4}$ alkyl, $C_{1-4}$ alkoxy, cyano, amino or nitro group.

8. A process for the production of a compound according to claim 1, comprising reacting a compound of formula II

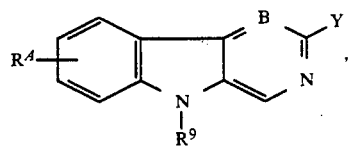

wherein,
$R^4$ and B have the above-mentioned meaning;
$R^9$ is a hydrogen or protecting group;
Y is a cyano or —CO—Z; and
Z is hydrogen, $C_{1-4}$ alkoxy, or an acid derivative;
with a metallo-organic compound R-Me; and optionally,
cleaving a trialkylsilyl group to a hydroxy group; or
etherifying a hydroxy group to $OR^5$; or
oxidizing $R^3$= ——CH(OH)R to the ketone, wherein R has the above-mentioned meaning; or
separating the isomers; or
forming the acid addition salts.

* * * * *

UNITED STATES PATENT AND TRADEMARK OFFICE
CERTIFICATE OF CORRECTION

PATENT NO. : 5,254,563
DATED : October 19, 1993
INVENTOR(S) : Andreas HUTH et al.

It is certified that error appears in the above-indentified patent and that said Letters Patent is hereby corrected as shown below:

Claim 1, column 10, line 67: After " $R^4$ is " and before " unsubstituted " insert - - hydrogen, $C_{1-4}$ alkyl or $C_{1-4}$ alkoxy-$C_{1-2}$ alkyl; and $R^3$ is -CO-R or -CHOH-R wherein R is an - -

Signed and Sealed this

Ninth Day of May, 1995

Attest:

BRUCE LEHMAN

*Attesting Officer*     *Commissioner of Patents and Trademarks*